United States Patent [19]

Nussbaum

[11] Patent Number: 4,834,654

[45] Date of Patent: May 30, 1989

[54] DENTAL PROSTHESIS APPLICATOR

[76] Inventor: William J. Nussbaum, 84-25 Smedley St., Jamaica, N.Y. 11435

[21] Appl. No.: 180,444

[22] Filed: Apr. 12, 1988

[51] Int. Cl.⁴ ............................................... A61C 3/00
[52] U.S. Cl. ....................................... 433/141; 433/3; 433/215; 433/229
[58] Field of Search ................ 433/3, 9, 26, 141, 215, 433/218, 229

[56] References Cited

U.S. PATENT DOCUMENTS

| | | | |
|---|---|---|---|
| 2,341,153 | 2/1944 | Myerson | 433/26 |
| 2,756,504 | 7/1956 | Levine | 433/26 |
| 3,521,355 | 7/1970 | Pearlman | 433/3 |
| 3,521,357 | 7/1970 | Berglund et al. | 433/26 |
| 4,449,928 | 5/1984 | von Weissenfluh | 433/229 |
| 4,540,408 | 9/1985 | Llyod | 604/294 |
| 4,618,325 | 10/1986 | Appelle | 433/26 |

Primary Examiner—John J. Wilson
Attorney, Agent, or Firm—Gottlieb, Rackman & Reisman

[57] ABSTRACT

A dental prosthesis applicator having an elongated flat handle and a flexible adhesive strip for retaining a dental prosthesis is provided. The handle includes along one end thereof an opaque element which is suitable for covering a substantial portion of the dental prosthesis held by the adhesive strip when the strip is flexed 180 degrees.

3 Claims, 1 Drawing Sheet

DENTAL PROSTHESIS APPLICATOR

BACKGROUND OF THE INVENTION

This invention relates to dental instrumentation, and more particularly to an applicator for use in applying a dental prosthetic device to a tooth.

For several years, dental prosthetic devices have been available to cover the front surface of a patient's tooth. More specifically, porcelain lamination veneers are often applied to the specially prepared surface of a tooth in order to repair and correct the appearance thereof. In order to apply such a veneer, the tooth is prepared by removing a portion of its front surface in a manner which is well-known to dentists and dental assistants. Then, an impression is made of the prepared tooth surface, and a porcelain laminated veneer is manufactured by a laboratory from the impression. The veneer is created with a surface that corresponds to the prepared surface of the tooth. Often, several teeth of the patient are prepared in this manner.

The laboratory delivers to the dentist one or more series of laminated veneers which are typically the size and shape of a small fingernail. The dentist then carries out a process of fitting and adjusting the veneer to the tooth.

As currently delivered by laboratories, these veneers have to be matched by the dentist to the particular tooth, and adhesives have to be applied to either the surface of the tooth or to the surface of the veneer, or to both, and appropriate adjustments made. Such adjustments require not only mechanical adjustment such as trimming the veneer, but also staining of the adhesive, or selecting an adhesive of the appropriate stain, so that the veneer applied to the tooth has the correct appearance.

Each of these stages requires manipulation of the veneer, during which it is presently the practice for the dentist to handle the veneer with his fingers.

The small size and delicacy of the veneer make this at best an awkward operation. Because of the dimensions of the prosthetic device involved, even a skilled dentist runs some risk of damaging the veneer, and there is the possibility of contamination of the adhesive.

Moreover, to complicate things, when curing the adhesive, it is necessary to illuminate the veneer with a high intensity light, for example, using a halogen lamp. This at times often causes undesirable shrinkage of the adhesive, which can create microcavities between the tooth and the veneer, greatly increasing the risk of failure of the procedure.

Accordingly, it is desirable to provide an applicator for use in applying dental prosthetic devices to a tooth which overcomes the above-discussed disadvantages.

SUMMARY OF THE INVENTION

Generally speaking, in accordance with the invention, a dental applicator which permits the dentist to have a simple means for manipulating the veneer during installation and which may be easily removed at the conclusion of the fitting is provided. The applicator consists of an elongated substantially flat handle having a first transparent element and a second opaque element that is continuous with the transparent element. The applicator also includes an adhesive surface integrally attached to the opaque element which is capable of being bent with respect to the long axis of the handle.

The opaque element is suitable for covering a substantial portion of the veneer which is adhered to the adhesive surface of the applicator when the adhesive surface is appropriately bent. This enables the exposure of only the exterior of the veneer, which prevents undesirable shrinkage of the applied adhesive during installation.

Accordingly, it is an object of the present invention to provide a simple applicator which may be used by the manufacturer of the prosthetic device or by a dentist.

It is another object of the invention to provide an applicator which may be appropriately labeled in order to indicate the identity of the patient and the location of the tooth for which the veneer was manufactured.

Still another object of the invention is to provide an applicator which is suitable for use with adhesives in order to be satisfactory for adhering veneers to a tooth.

Yet a further object of the invention is to provide an applicator which does not interfere with the visibility of the veneer during the application process.

Yet another object of the invention is to provide an applicator which prevents undesirable shrinkage of the adhesive during the installation process.

Still a further object of the invention is to prevent microcavities between the tooth and the veneer during the curing process.

Still other objects and advantages of the invention will in part be obvious and will in part be apparent from the following description.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the invention, reference is made to the following description taken in connection with the accompanying drawings, in which.

DETAILED DESCRIPTION OF PREFERRED EMBODIMENT

The applicator in accordance with the invention has a preferred embodiment which is best illustrated in FIGS. 1-5. The applicator comprises a transparent elongated substantially flat handle portion 13 which may be stamped out of any transparent material suitable for the installation purpose, such as plastic. The handle is made transparent so that it does not interfere with the view by the dentist of the patient's mouth during the application process. The handle portion 13 is provided at one end with an opaque element 15, which as described in more detail below prevents the transmission of light to most of the veneer during the installation process.

Figure 1:
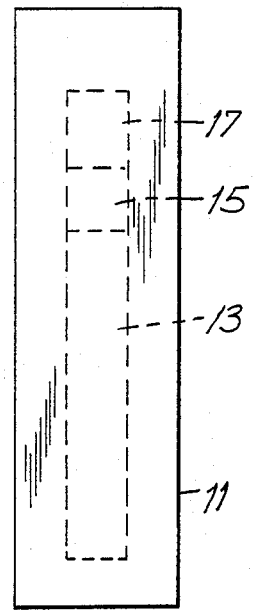
FIG. 1 is a top plan view of the applicator in accordance with the invention shown stored in a sterile package.
Figure 2:
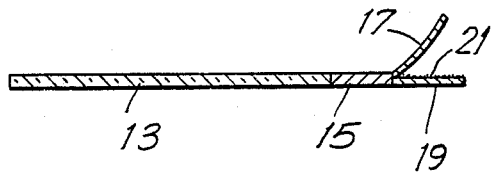
FIG. 2 is a cross-sectional view of the applicator shown in FIG. 1 and illustrating the removal of a protective strip from the adhesive element.

A transparent adhesive strip 19 is attached to the end of opaque strip 15 and is provide with a protective strip, or backing 17. Adhesive strip 19 is flexible so that it can be bent with respect to handle portion 13 and opaque strip 15. After removing the applicator from a sterile package 11, shown in FIG. 1, backing 17 is separated from adhesive strip 19, as shown in FIG. 2, in order to expose an adhesive surface 21 on one side of strip 19.

Figure 3:
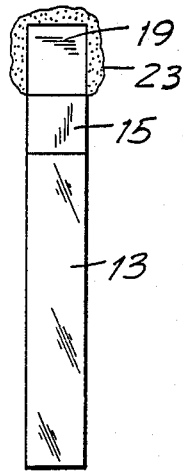
FIG. 3 is a top plan view of the applicator of FIG. 1 as applied to a veneer.

In FIG. 3, a veneer 23 is shown adhered to the applicator by contacting the veneer with adhesive surface 21 of adhesive strip 19.

Figure 4:
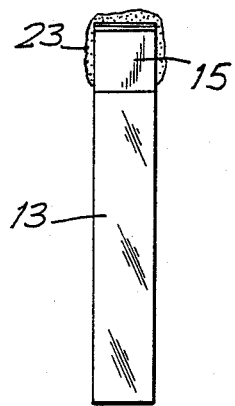
FIG. 4 is a bottom plan view of the applicator of FIG. 2 showing the adhesive element flexed to permit application of the veneer to a tooth.
Figure 5:
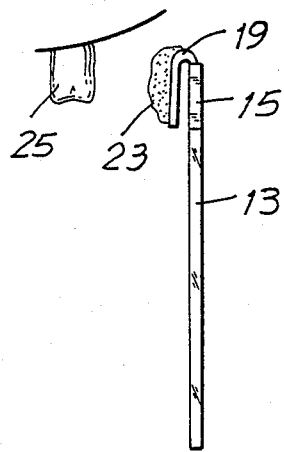
FIG. 5 is a side view of the applicator shown in FIG. 4 showing the veneer approaching the tooth of a patient during the installation process.

During installation, veneer 23 is fixed substantially 180 degrees, as shown in FIGS. 4 and 5, which causes opaque strip 15 to cover most of veneer 23, but still leave exposed the exterior of veneer 23. Therefore, when the applicator is used to apply veneer 23 to a tooth 25, as shown in FIG. 5, only the exterior of veneer 23 is exposed. Once an adhesive is applied to either the surface of the tooth or the veneer, an appropriate illumination source, such as a high intensity halogen lamp, may be used to cure and fix the adhesive. Since only the exterior of the veneer is exposed, shrinkage of most of the adhesive is prevented.

Once curing and fixing of the adhesive are underway, the applicator may be removed in order to enable the fixing process to be completed.

Another advantage of the present invention is that the applicator may receive a lettering indicia on the handle to permit the identification of the patient and the particular tooth for which the veneer was manufactured.

Although one particular embodiment of this invention has been described in detail, it is clear that other equivalent embodiments should be also included within the scope of this invention.

For example, it is also contemplated that the adhesive means of the applicator need not be a separate adhesive strip. Instead, the handle may be provided with a flexible end to which an adhesive is attached.

It will thus be seen that the objects set forth above, among those made apparent from the preceeding description, are efficiently obtained and, since certain changes may be made in the above article without departing from the spirit and scope of the invention, it is intended that all matter contained in the above description and shown in the accompanying drawings shall be interpreted as illustrative and not in a limiting since.

It is also to be understood that the following claims are intended to cover all of the generic and specific features of the invention herein described and all statements of the scope of the invention which, as a matter of language, might be said to fall therebetween.

What is claimed is:

1. An applicator for a dental prosthesis which is applied to a tooth using an adhesive comprising:
    an elongated substantially flat handle means, said handle means including a first transparent element and a second opaque element continuous with said transparent element and suitable for covering a substantial portion of said prosthesis; and
    an adhesive means for supporting said dental prosthesis integrally attached to said opaque element and capable of being bent with respect to the longitudinal axis of said handle means in order to mask most of the prosthesis and prevent undesirable shrinkage of the adhesive during initial curing.

2. The applicator of claim 1, wherein said adhesive means comprises a transparent adhesive strip.

3. The applicator of claim 2, further including a protective strip covering said adhesive strip.

* * * * *